US012296119B2

(12) United States Patent
Garrison et al.

(10) Patent No.: US 12,296,119 B2
(45) Date of Patent: May 13, 2025

(54) SOFT PUSH TABS FOR CATHETER ADAPTER

(71) Applicant: Becton, Dickinson and Company, Franklin Lakes, NJ (US)

(72) Inventors: Michael Garrison, La Jolla, CA (US); Bart D. Peterson, Farmington, UT (US); Ralph L. Sonderegger, Farmington, UT (US); Jonathan Karl Burkholz, Salt Lake City, UT (US); Nathan Mitchell, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 18/642,514

(22) Filed: Apr. 22, 2024

(65) Prior Publication Data

US 2024/0277973 A1    Aug. 22, 2024

Related U.S. Application Data

(63) Continuation of application No. 16/601,320, filed on Oct. 14, 2019, now Pat. No. 11,964,117, which is a continuation of application No. 15/286,159, filed on Oct. 5, 2016, now Pat. No. 10,814,106.

(60) Provisional application No. 62/296,383, filed on Feb. 17, 2016, provisional application No. 62/296,385, filed on Feb. 17, 2016, provisional application No. (Continued)

(51) Int. Cl.
| | |
|---|---|
| A61M 25/06 | (2006.01) |
| A61M 5/158 | (2006.01) |
| A61M 5/162 | (2006.01) |
| A61M 25/00 | (2006.01) |

(Continued)

(52) U.S. Cl.
CPC ........ *A61M 25/0606* (2013.01); *A61M 5/158* (2013.01); *A61M 5/1626* (2013.01); *A61M 25/0097* (2013.01); *A61M 25/0113* (2013.01); *A61M 25/0631* (2013.01); *A61M 25/0637* (2013.01); *A61M 2005/1585* (2013.01); *A61M 2025/0266* (2013.01); *A61M 25/0693* (2013.01)

(58) Field of Classification Search
CPC .... A61M 2005/1586; A61M 2005/325; A61M 25/0625; A61M 5/158; A61M 5/3275; A61M 25/0606; A61M 5/1626; A61M 25/0097; A61M 25/0113
USPC ..................................................... 604/164.07
See application file for complete search history.

(56) References Cited

U.S. PATENT DOCUMENTS

2011/0054403 A1* 3/2011 Tanabe ................. A61M 5/158
604/164.01

* cited by examiner

*Primary Examiner* — Phillip A Gray
(74) *Attorney, Agent, or Firm* — Kirton McConkie; Whitney Blair; Kevin Stinger

(57) ABSTRACT

An IV catheter system may have a catheter component and a needle component. The catheter component may have a catheter hub, a cannula extending distally from the catheter hub, and a push feature extending outward from the catheter hub. The push feature may have an outer surface that receives contact from a digit to move the IV catheter system from an insertion configuration, in which the needle is within the cannula, to a fluid delivery configuration, in which the needle is outside the catheter hub. The needle component may have a needle hub and a needle extending distally from the needle hub along an axis. The push feature may be formed of a flexible material that causes the push feature, in response to pressure exerted on the outer surface by a dressing securing the catheter component to a patient, to deflect the outer surface toward the cannula axis.

20 Claims, 10 Drawing Sheets

Related U.S. Application Data

62/247,599, filed on Oct. 28, 2015, provisional application No. 62/247,621, filed on Oct. 28, 2015, provisional application No. 62/247,617, filed on Oct. 28, 2015, provisional application No. 62/247,624, filed on Oct. 28, 2015, provisional application No. 62/247,596, filed on Oct. 28, 2015, provisional application No. 62/247,607, filed on Oct. 28, 2015, provisional application No. 62/247,626, filed on Oct. 28, 2015.

(51) Int. Cl.
*A61M 25/01* (2006.01)
*A61M 25/02* (2006.01)

SOFT PUSH TABS FOR CATHETER ADAPTER

RELATED APPLICATIONS

This application is a continuation of U.S. patent application Ser. No. 16/601,320, filed Oct. 14, 2019, which is a continuation of U.S. patent application Ser. No. 15/286,159, filed Oct. 5, 2016, which claims the benefit of U.S. Provisional Patent Application No. 62/247,596, which was filed on Oct. 28, 2015, U.S. Provisional Patent Application No. 62/296,383, which was filed on Feb. 17, 2016, U.S. Provisional Patent Application No. 62/247,599, which was filed Oct. 28, 2015, U.S. Provisional Patent Application No. 62/247,617, which was filed on Oct. 28, 2015, U.S. Provisional Patent Application Ser. No. 62/247,607, which was filed Oct. 28, 2015, U.S. Provisional Patent Application Ser. No. 62/247,621, which was filed Oct. 28, 2015, U.S. Provisional Patent Application Ser. No. 62/247,624, which was filed Oct. 28, 2015, U.S. Provisional Application No. 62/247,626, which was filed on Oct. 28, 2015, and U.S. Provisional Application No. 62/296,385, which was filed on Feb. 17, 2016, each of which is incorporated herein by reference in their entirety.

BACKGROUND

The present invention is generally directed to systems and methods for intravenous ("IV") delivery, by which fluids can be administered directly to the vascular system of a patient. More particularly, the present invention is directed to IV catheter systems and methods that facilitate insertion into the patient and/or motion from an insertion configuration to a fluid delivery configuration in which fluid can be delivered to the patient through the IV catheter system. An IV catheter system according to the invention is used broadly herein to describe components used to deliver the fluid to the patient, for use in arterial, intravenous, intravascular, peritoneal, and/or non-vascular administration of fluid. Of course, one of skill in the art may use an IV catheter system to administer fluids to other locations within a patient's body.

Known IV catheter systems and methods have a number of deficiencies. Many such systems require the clinician to use two hands to position the IV catheter system and/or insert the needle into the fluid delivery location on the patient (for example, the vein into which fluid is to be delivered). Further, many such systems require the clinician to use two hands to move the IV catheter system from the insertion configuration to a fluid delivery configuration, in which the needle is removed from the cannula to permit fluid to be delivered to the vein through the cannula. Thus, the clinician is required to stabilize the patient's arm or other body part having the fluid delivery location prior to insertion of the IV catheter system. As a result, extra time is required for the clinician to initiate transfusion. Further, the clinician is unable to perform any other task, such as stabilizing or reassuring the patient, during insertion and/or motion to the fluid delivery configuration.

Additionally, known IV systems, in many instances, have protruding rigid elements that extend outward from the wound site when the needle is in place. Such rigid elements can snag on or puncture adhesives, bandages, or other dressings such as those that keep the needle in position.

Accordingly, there is a need for IV catheter systems and methods that facilitate IV catheter system placement, insertion, and/or preparation for fluid delivery without the need for rigid protruding elements. There is a further need for such IV catheter systems that are inexpensive, easy to manufacture, and versatile.

BRIEF SUMMARY

Embodiments of the present invention are generally directed to an IV catheter system designed to protect dressings used to keep the catheter component in place. In some embodiments, the IV catheter system may be inserted and moved to the fluid delivery configuration with only one hand.

In one embodiment, the IV catheter system may have a catheter component and a needle component. The catheter component may have a catheter hub with a catheter hub distal end and a catheter hub proximal end. The catheter hub may be shaped to define a chamber extending between the catheter hub distal end and the catheter hub proximal end, and a needle port at the catheter hub proximal end that provides access to the chamber. The catheter component may also have a cannula extending distally from the catheter hub distal end along a cannula axis, and a push feature extending outward from the catheter hub. The push feature may have an outer surface positioned to receive contact from a digit such that the digit urges the IV catheter system to move from the insertion configuration to the fluid delivery configuration. The needle component may have a needle hub with a needle hub distal end and a needle hub proximal end, and a needle extending distally from the needle hub distal end along a needle axis. In an insertion configuration, the needle may be positioned within the cannula and the needle hub distal end may be seated in the needle port. In a fluid delivery configuration, the needle may be positioned outside the catheter hub. The push feature may be formed of a flexible material that causes the push feature, in response to pressure exerted on the outer surface by a dressing securing the catheter component to a patient, to flex such that the outer surface deflects toward the cannula axis.

The needle component may further have a grip extending from the needle hub, generally parallel to the needle axis. The grip may have a pull feature. The push feature and the pull feature may be positioned to receive contact from one or more additional digits of the same hand as the digit to urge the IV catheter system to move from the insertion configuration to the fluid delivery configuration.

The catheter component may further have a securement platform with a first wing extending from the catheter hub, generally parallel to the cannula axis such that, in the fluid delivery configuration, the first wing rests on skin of a patient receiving fluid through the IV catheter system. In the insertion configuration, the first wing and the grip may be generally parallel to each other and may be positioned in abutting relation to each other. During motion of the IV catheter system from the insertion configuration to the fluid delivery configuration, the grip may slide along the first wing.

The push feature may be a tab positioned closer to the catheter hub distal end than to the catheter hub proximal end. The catheter component may further have a pad positioned proximate the catheter hub proximal end. The pad may have a surface texture selected to provide frictional engagement with the digit or with another digit of the same hand as the digit. Alternatively, the push feature may be a tab positioned generally equidistant from the catheter hub distal end and the catheter hub proximal end.

The outer surface may be on a first ridge oriented substantially perpendicular to the cannula axis. The push feature may further have a plurality of additional ridges oriented generally parallel to the first ridge.

The push feature may be formed of a material having a lower durometer than the catheter hub. The catheter hub may further have an opaque component molded as a single piece with the push feature. The catheter hub may further have a translucent component defining at least one wall of the chamber such that blood within the chamber is visible from outside the chamber through the at least one wall.

The push feature may have a plurality of adjacent surfaces adjacent to and angled relative to the outer surface. Further, the push feature may have a plurality of rounds positioned to join the outer surface with each of the adjacent surfaces in a manner that avoids puncturing the dressing.

In another embodiment, an IV catheter system may have a catheter component and a needle component. The catheter component may have a catheter hub with a catheter hub distal end and a catheter hub proximal end. The catheter hub may have a translucent component defining at least one wall of a chamber extending between the catheter hub distal end and the catheter hub proximal end, and a needle port at the catheter hub proximal end that provides access to the chamber. The catheter component may also have a cannula extending distally from the catheter hub distal end along a cannula axis, and a tab extending outward from the catheter hub. The tab may be formed of a material having a lower durometer than the translucent component. The needle component may have a needle hub with a needle hub distal end and a needle hub proximal end, and a needle extending distally from the needle hub distal end along a needle axis. In an insertion configuration, the needle may be positioned within the cannula and the needle hub distal end may be seated in the needle port. In a fluid delivery configuration, the needle may be positioned outside the catheter hub.

The needle component may further have a grip extending from the needle hub, generally parallel to the needle axis, the grip comprising a pull feature. The tab and the pull feature may be positioned to receive contact from one or more digits of a single hand to urge the IV catheter system to move from the insertion configuration to the fluid delivery configuration. The catheter component may further have a securement platform with a first wing extending from the catheter hub, generally parallel to the cannula axis such that, in the fluid delivery configuration, the first wing rests on skin of a patient receiving fluid through the IV catheter system. In the insertion configuration, the first wing and the grip may be generally parallel to each other and may be positioned in abutting relation to each other. During motion of the IV catheter system from the insertion configuration to the fluid delivery configuration, the grip may slide along the first wing.

The tab may have an outer surface positioned to receive contact from a digit such that the digit urges the IV catheter system to move from the insertion configuration to the fluid delivery configuration, and a plurality of adjacent surfaces adjacent to and angled relative to the outer surface. Further, the tab may have a plurality of rounds positioned to join the outer surface with each of the adjacent surfaces in a manner that avoids puncturing a dressing securing the catheter component to a patient.

The catheter hub may further have an opaque component formed as a single piece with the tab. The opaque component may cooperate with the translucent component to define the chamber.

In another embodiment, an IV catheter system may have a catheter component and a needle component. The catheter component may have a catheter hub with a catheter hub distal end and a catheter hub proximal end. The catheter hub may be shaped to define a chamber extending between the catheter hub distal end and the catheter hub proximal end, and a needle port at the catheter hub proximal end that provides access to the chamber. The catheter component may also have a cannula extending distally from the catheter hub distal end along a cannula axis, and a push feature extending outward from the catheter hub. The push feature may have an outer surface positioned to receive contact from a digit such that the digit urges the IV catheter system to move from the insertion configuration to the fluid delivery configuration, a plurality of adjacent surfaces adjacent to and angled relative to the outer surface, and a plurality of rounds positioned to join the outer surface with each of the adjacent surfaces in a manner that avoids puncturing a dressing securing the catheter component to a patient. The needle component may have a needle hub with a needle hub distal end and a needle hub proximal end, a needle extending distally from the needle hub distal end along a needle axis, and a grip extending from the needle hub, generally parallel to the needle axis, the grip comprising a pull feature. In an insertion configuration, the needle may be positioned within the cannula and the needle hub distal end may be seated in the needle port. In a fluid delivery configuration, the needle may be positioned outside the catheter hub. The push feature may be formed of a flexible material that causes the push feature, in response to pressure exerted on the outer surface by the dressing, to flex such that the outer surface deflects toward the cannula axis. The push feature and the pull feature may be positioned to receive contact from one or more additional digits of the same hand as the digit to urge the IV catheter system to move from the insertion configuration to the fluid delivery configuration. The catheter component may further have a securement platform with a first wing extending from the catheter hub, generally parallel to the cannula axis such that, in the fluid delivery configuration, the first wing rests on skin of a patient receiving fluid through the IV catheter system. In the insertion configuration, the first wing and the grip may be generally parallel to each other and may be positioned in abutting relation to each other. During motion of the IV catheter system from the insertion configuration to the fluid delivery configuration, the grip may slide along the first wing. The push feature may be formed of a material having a lower durometer than the catheter hub.

The push feature may have a tab positioned closer to the catheter hub distal end than to the catheter hub proximal end. The catheter component may further have a pad positioned proximate the catheter hub proximal end. The pad may have a surface texture selected to provide frictional engagement with the digit or with another digit of the same hand as the digit.

The catheter hub may further have an opaque component molded as a single piece with the push feature, and a translucent component defining at least one wall of the chamber. Blood within the chamber may be visible from outside the chamber through the at least one wall.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" refers to a location on the device that is closest to the clinician using the device and farthest from the patient in connection with whom the device is used when the device is used in its normal operation. Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device. Further, as used herein, a "cannula" is a tube that can be inserted into the body for delivery and/or removal of fluid. A cannula may be rigid or flexible, and may be formed of any material, including but not limited to metals, ceramics, polymers, elastomers, and composite materials.

Figure 1:
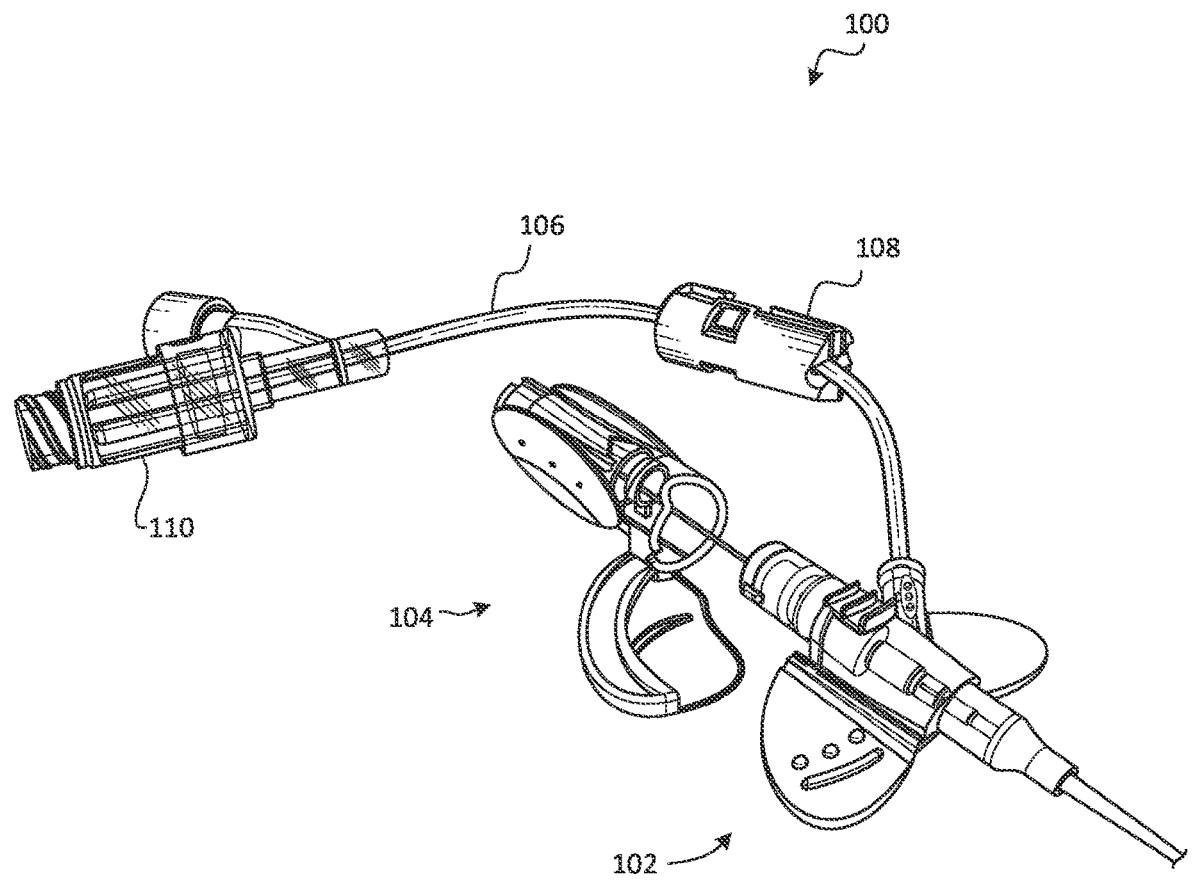
FIG. 1 is a perspective view of an IV catheter system according to one embodiment.

FIG. 1 is a perspective view of an IV catheter system 100 according to one embodiment. The IV catheter system 100 may be connected to a supply of fluid to be infused. The fluid supply (not shown) may include a bag of blood or medication to be delivered to the patient, a drip chamber that regulates flow of the fluid to the IV catheter system 100, and/or other components involved with the supply of fluid to the IV catheter system 100. The IV catheter system 100 may have a number of components, as shown in the exemplary embodiment of FIG. 1. These components may include a catheter component 102, a needle component 104, an extension tube 106, a clamp 108, a Y adapter 110, and/or a flash receptacle (not shown).

The catheter component 102 may be inserted into the fluid delivery location in the patient in order to convey the fluid to the patient. The needle component 104 may facilitate insertion of the catheter component 102 to the fluid delivery location. The extension tube 106 may convey the fluid to the catheter component 102. The clamp 108 may be used to manually block fluid flow to the catheter component 102 when it is desired to stop or pause fluid delivery. The Y adapter 110 may have luer lock fittings that are readily connected to the fluid supply and/or other fluid-carrying components, for example, via connection to a complementary luer lock (not shown) of the fluid supply or other fluid components. The flash receptacle is an optional component, and may have a flash chamber that receives blood when the IV catheter system has been positioned to access a blood vessel. The flash receptacle may thus indicate proper insertion of the IV catheter system 100.

As embodied in FIG. 1, the IV catheter system 100 may be an integrated IV catheter system, as the extension tube 106 is pre-attached to the catheter component 102. In other embodiments, IV catheter systems of various open, integrated, and/or safety integrated configurations may be used.

Figure 2A:
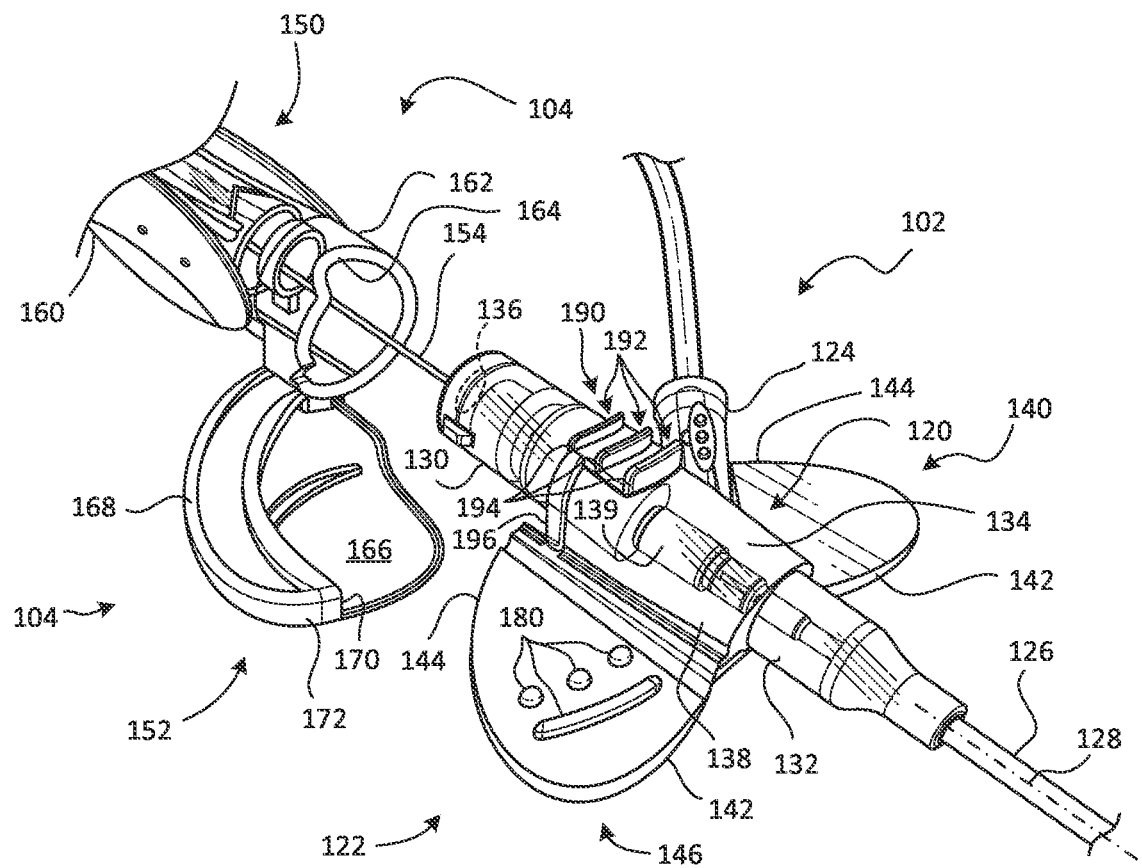
FIGS. 2A and 2B are top and bottom perspective views, respectively, of a portion of the IV catheter system of FIG. 1.
Figure 2B:
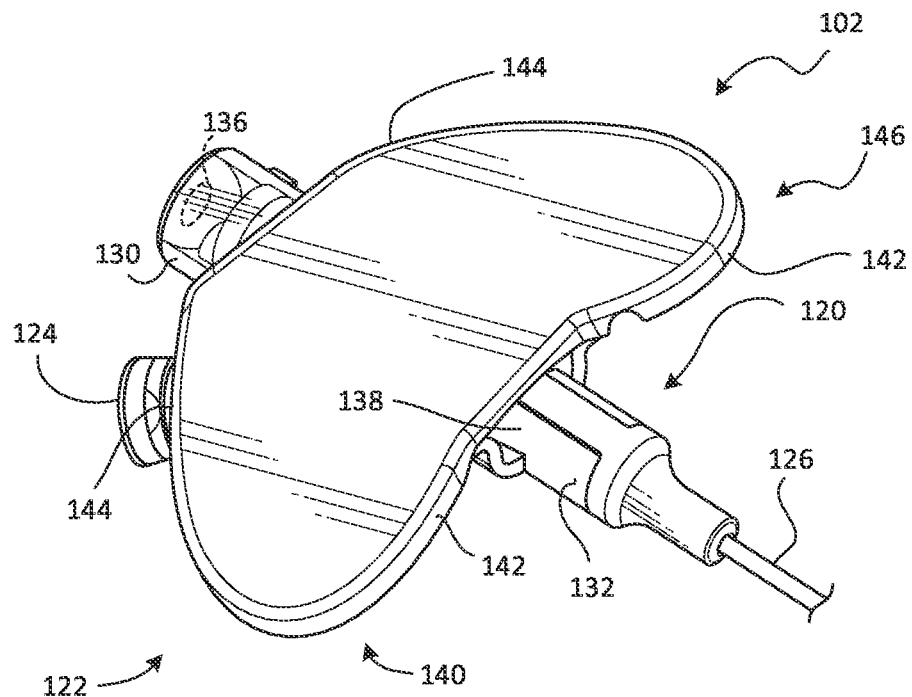

Referring to FIGS. 2A and 2B, top and bottom perspective views, respectively, depict portions of the IV catheter system 100 of FIG. 1. The catheter component 102 may have various parts, which may include a catheter hub 120, a securement platform 122, an extension tubing junction 124, and a cannula 126. The catheter hub 120 may have a generally tubular and/or hollow conical configuration, and may have a proximal end 130 and a distal end 132. The catheter hub 120 may have a translucent component 138 that is shaped to define a chamber 134 through which the fluid flows to reach the fluid delivery location. The catheter hub 120 may have a needle port 136 at the proximal end 130. The chamber 134 may contain a septum 139 that is designed to block flow of blood and/or the fluid to be delivered from the chamber 134 through the needle port 136. The cannula 126 may be secured to the distal end 132 of the catheter hub 120, and may extend proximally of the distal end 132 along a cannula axis 128.

The securement platform 122 may have a generally planar configuration designed to permit the securement platform 122 to be secured to the skin of the patient, proximate the fluid delivery location, to keep the catheter component 102 securely in place as fluid delivery takes place. As embodied in FIG. 1, the securement platform 122 may have a first wing 140 with a generally planar shape. The first wing 140 may be fixedly secured to the catheter hub 120, and may have a rounded profile when viewed from along a direction perpendicular to the securement platform 122. The first wing 140 may have a leading edge 142 proximate the distal end 132 and a trailing edge 144 proximate the proximal end 130 of the catheter hub 120.

The securement platform 122 may also include a second wing 146, which may be coplanar with the first wing 140. The second wing 146 may extend away from the catheter hub 120 in a direction generally opposite to that of the first wing 140, and may optionally be symmetrical to the first wing 140. The second wing 146 may also have a leading edge 142 proximate the distal end 132 and a trailing edge 144 proximate the proximal end 130 of the catheter hub 120. The first wing 140 and the second wing 146 may, together, provide a variety of options for gripping the catheter component 102 for insertion and/or motion to the fluid delivery configuration.

The first wing 140 and the second wing 146 may not be coplanar with the cannula axis 128 but may, instead, be offset from the cannula axis 128. Thus, the first wing 140 and the second wing 146 may not intersect the midline of the catheter hub 120. The first wing 140 may optionally be integrated with and/or secured to the extension tubing junction 124 such that the extension tubing junction 124 divides the first wing 140 into a leading portion and a trailing portion having the trailing edge 144. Thus, the axis of the extension tubing junction 124 may be coplanar with the cannula axis 128, or may alternatively be coplanar with the first wing 140 and offset from the cannula axis 128.

The needle component 104 may have a needle hub 150, a grip 152, and a needle 154. The needle hub 150 may be detachably coupled to the catheter hub 120 of the catheter component 102. The grip 152 may extend outward from the needle hub 150. The needle 154 may be removably positioned within the cannula 126 such that the needle 154 facilitates the process of accessing the fluid delivery location (for example, a vein) and proper positioning of the cannula 126 to deliver the fluid to the fluid delivery location. The needle 154 may extend distally from the needle hub 150 along a needle axis, which maybe coincident with the cannula axis 128 when the IV catheter system 100 is in an insertion configuration. In FIGS. 1 and 2A, the IV catheter system 100 is between the insertion configuration and the fluid delivery configuration, with the needle component 104 partially withdrawn from the proximal end 130 of the catheter hub 120.

The needle hub 150 may have a generally tubular shape with a proximal end 160 and a distal end 162. The distal end 162 may have a recess 164 that makes it easier for a clinician to grip the catheter component 102, as will be shown and described subsequently.

The grip 152 may have a generally planar shape that extends outward from the needle hub 150. When viewed from a direction perpendicular to the grip 152, the grip 152 may have a curved shape that conforms to the shape of the second wing 146 of the securement platform 122 of the catheter component 102.

Specifically, the grip 152 may further have a medial portion 166 and a lateral portion 168 separated from the medial portion 166 by a wall 170. The wall 170 may be shaped to match the outer contour of the second wing 146 such that, when the IV catheter system 100 is in the insertion configuration, the second wing 146 nests against the medial portion 166 and the wall 170. The thickness of the lateral portion 168 may be greater than that of the medial portion 166 such that, in the insertion configuration, the top surface of the lateral portion 168 is flush with the top surface of the second wing 146. The grip 152 may also have a leading edge 172, which may operate as a "pull surface" on which a digit (i.e., a finger or thumb) of a clinician can be placed to urge the needle component 104 to move proximally with respect to the catheter component 102, as will be described subsequently.

The grip 152 and the securement platform 122 may each have one or more grip features 180, which may facilitate gripping the catheter component 102 and/or the needle component 104, and/or moving the IV catheter system 100 between the insertion configuration and the fluid delivery configuration. The grip features 180 may have various shapes and locations, which may include bumps, ridges, and/or combinations thereof.

Further, the catheter component 102 may have a tab 190, which may operate as a push feature, as described below. The tab 190 may extend outward from the cannula axis 128 along a direction generally perpendicular to the cannula axis 128. Specifically, the tab 190 may have a plurality of ridges 192, each of which extends away from the cannula axis 128, along directions generally perpendicular to the cannula axis 128. Each of the ridges 192 may be oriented generally transverse to the cannula axis 128, so as to define a push feature 194 with a relatively broad, accessible shape. The push features 194 may be the proximally-facing surface of the ridges 192.

In some embodiments, the tab 190 may be formed as a single piece with the securement platform 122, and may be connected to the securement platform 122 by arms 196 that extend around the periphery of the catheter hub 120, from the tab 190 to the securement platform 122. Thus, the tab 190 and the securement platform 122 may be formed of the same material by injection molding or other processes. This material may be an elastomeric or other low-durometer material that is relatively gentle against the patient's skin and/or dressings used to keep the catheter component 102 in place during fluid delivery. For example, some embodiments of the present invention comprise a low-durometer material having a durometer hardness of from approximately 30

Shore A to approximately 90 Shore D. In some embodiments, a low-durometer material comprises a durometer hardness of from approximately 50 Shore A to approximately 90 Shore D. In some embodiments, the tab 190 and/or the securement platform 122 may be formed of a thermoplastic elastomer (TPE) or the like.

Figure 3:
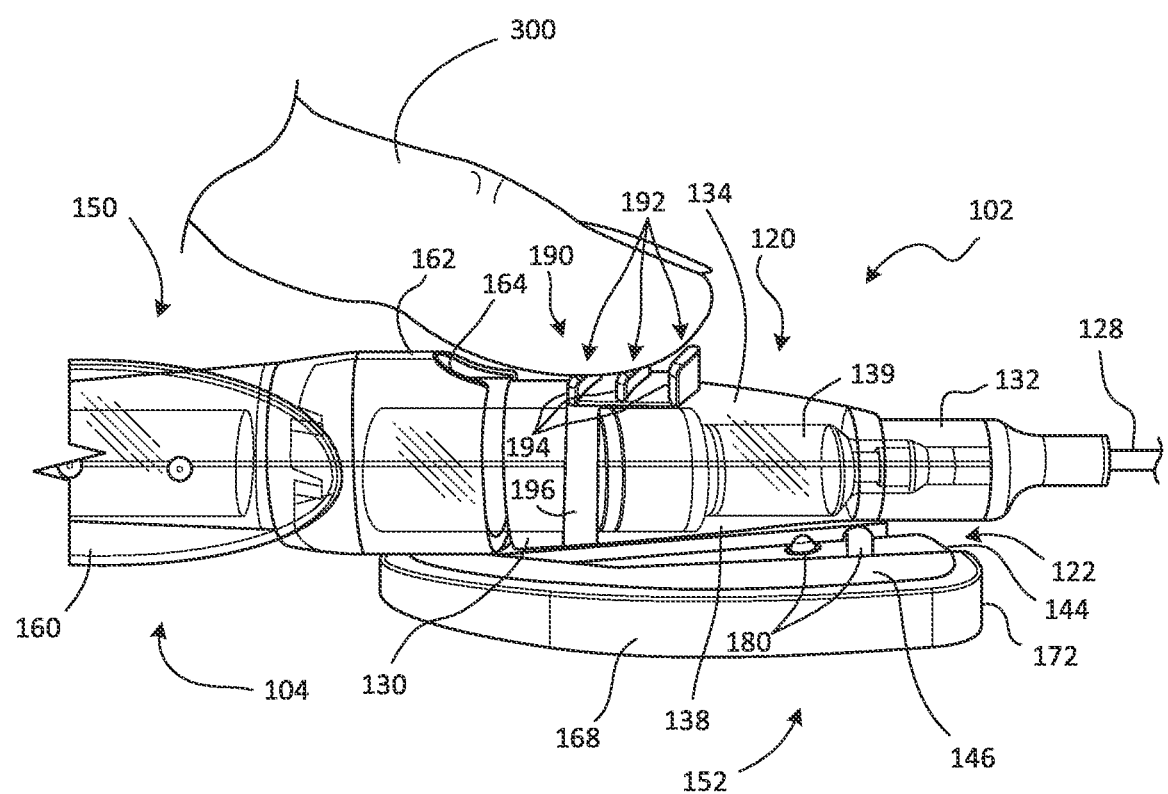
FIG. 3 is a side elevation view of the IV catheter system of FIG. 1 in the insertion configuration, with a finger positioned on the tab to urge the IV catheter system to move from the insertion configuration to the fluid delivery configuration.

Referring to FIG. 3, a side elevation view depicts the IV catheter system 100 of FIG. 1 in the insertion configuration, with a finger 300 positioned on the tab 190 to urge the IV catheter system 100 to move from the insertion configuration to the fluid delivery configuration. In the insertion configuration depicted in FIG. 3, needle hub 150 of the needle component 104 may be positioned adjacent to the proximal end 130 of the catheter hub 120 of the catheter component 102 such that the needle 154 extends through the cannula 126 to provide a sharpened tip (not shown) for piercing tissue, and to support the cannula 126 during insertion of the cannula 126 through tissue. Thus, in the insertion configuration, the IV catheter system 100 may be readily insertable to position the cannula 126 in the fluid delivery location. In the insertion configuration, the needle 154 may also pass through the septum 139 of the catheter component 102.

In the fluid delivery configuration, the needle component 104 may be withdrawn and positioned elsewhere so as to avoid interfering with the operation of the catheter component 102. The septum 139 may define a seal within the chamber 134 that prevents leakage of fluids from the needle port 136. Thus, fluid may flow to the patient through the cannula 126 in a relatively unimpeded manner.

The IV catheter system 100 may be inserted into position by, with the IV catheter system in the insertion configuration, positioning the tip of the cannula 126 and the tip of the needle 154 (not shown) proximate the fluid delivery location (for example, the patient's vein). The securement platform 122 may be placed on the patient's skin, proximate the fluid delivery location and/or held in the clinician's hand. The catheter component 102 and the needle component 104 may be advanced to push the cannula 126 until the tip of the needle 154 and the tip of the cannula 126 penetrate the surrounding tissue to reach the fluid delivery location.

If desired, the catheter component 102 may be advanced by pushing a push feature of the catheter component 102. The "push feature" is a feature with a surface that is generally proximally-oriented, or is textured or otherwise provides sufficient frictional engagement with a clinician's digit to receive distally-oriented force from the digit. Thus, the clinician may urge the catheter component 102 and the needle component 104, together, distally to position the cannula 126 at the fluid delivery location.

The tab 190 may operate as a pull feature, as mentioned above, and may provide a plurality of push features 194. Thus, a clinician may position a finger or thumb on the tab 190 during insertion of the IV catheter system 100, and may exert pressure on the push features to urge the catheter component 102 to move distally.

Once the tip of the cannula 126 has reached the fluid delivery location, the IV catheter system 100 may be moved to the fluid delivery configuration. This may be done by withdrawing the needle component 104 proximally from the catheter component 102. This may cause the needle 154 to be withdrawn proximally from the cannula 126, and then from the septum 139. The needle 154 may pass out of the chamber 134 through the needle port 136, thus completing motion of the IV catheter system 100 to the fluid delivery configuration. Fluid flow to the fluid delivery location may now be accomplished by urging the fluid to flow through the extension tube 106, into the chamber 134, and through the cannula 126 to the fluid delivery location.

The IV catheter system 100 may advantageously be designed to facilitate insertion to the fluid delivery location with a single hand. For example, during insertion, the clinician may, with one hand, hold the catheter component 102 and the needle component 104, for example, by grasping the securement platform 122 and the grip 152. The clinician may then, with the same hand, apply gentle pressure to one or more push features of the catheter component 102 (for example, the trailing edge 144 of the first wing 140 and/or the second wing 146) to urge the tip of the cannula 126 to penetrate the patient's skin and ultimately reach the fluid delivery location. If desired, one or more locking features (not shown) may be used to hold the catheter component 102 and the needle component 104 together until the clinician applies a threshold force to move the IV catheter system 100 from the insertion configuration to the fluid delivery configuration.

The IV catheter system 100 may be designed to provide visual confirmation of proper placement in a blood vessel. For example, the translucent component 138 of the catheter hub 120 may be translucent to provide visibility into the chamber 134. Thus, when the tip of the cannula 126 enters a vein, the resulting blood flow, or "flash," may be visible through the wall of the chamber 134 defined by the translucent component 138 as the blood enters the chamber 134. The extension tubing junction 124 and the extension tube 106 may also, optionally, be translucent. In some embodiments, the flash may extend through the extension tube 106 to the Y adapter 110. The Y adapter 110 may be coupled to the fluid supply in a manner that substantially prevents blood leakage. Further, a flash receptacle (not shown) may indicate flash by receiving blood within a flash chamber.

Further, the IV catheter system 100 may advantageously be designed to facilitate motion from the insertion configuration to the fluid delivery configuration with a single hand. For example, the clinician may, with a single hand, which may be the same hand used to insert the IV catheter system 100 into the fluid delivery location, grasp the catheter component 102 and the needle component 104 and withdraw the needle component 104 proximally from the catheter component 102. The catheter component 102 may be left substantially in place so that only the needle component 104 moves significantly to move the IV catheter system 100 from the insertion configuration to the fluid delivery configuration.

This may be done by placing digits of the hand to contact the pull surface(s) of the needle component 104 and the push feature(s) of the catheter component 102, and then with those digits, pulling the needle component 104 proximally while pushing the catheter component 102 distally to keep it from moving proximally with the needle component 104. For example, the push features 194 of the tab 190, the trailing edge 144 of the first wing 140, and/or the trailing edge 144 of the second wing 146 may act as push features, while the leading edge 172 of the grip 152 may act as a pull surface. The clinician may place one or more fingers on the leading edge 172 of the grip 152 and pulling proximally, while pushing with a thumb and/or one or more other fingers on the push features 194 of the tab 190, the trailing edge 144 of the first wing 140, and/or the trailing edge 144 of the second wing 146. Thus, the catheter component 102 may be kept in place with the tip of the cannula 126 at the fluid delivery location while the needle component 104 is withdrawn proximally from the catheter component 102 to unblock the fluid delivery path to the fluid delivery location.

The relative positions of the pull and push features may facilitate single-handed operation in the manner described above. If desired, the coupling of the needle hub 150 with the catheter hub 120 may be such that the needle hub 150 is rotatable relative to the catheter hub 120 while the IV catheter system 100 is in the insertion configuration. Thus, the clinician may, with the hand, rotate the grip 152 to an orientation that is most comfortable for pulling on the leading edge 172, prior to pulling on the leading edge 172 and pushing on the push features 194 of the tab 190, the trailing edge 144 of the first wing 140, and/or the trailing edge 144 of the second wing 146. For example, the clinician may optionally be able to rotate the grip 152 of the needle component 104 such that the second wing 146 rotates away from the medial portion 166 of the grip. This may provide more room for the clinician's digits to engage the leading edge 172, the trailing edge 144 of the first wing 140, and/or the trailing edge 144 of the second wing 146.

The septum 139 may have a "low friction" or "low drag" design configured to provide relatively low resistance to withdrawal of the needle 154 proximally through the septum, which occurs as the IV catheter system 100 transitions from the insertion configuration to the fluid delivery configuration. The resistance to withdrawal of the needle 154 through the septum may be sufficiently low that the clinician can relatively easily move the IV catheter system 100 from the insertion configuration to the fluid delivery configuration with only a single hand. In some embodiments, the resistance to withdrawal may be, on average, less than about 50 gf.

Figure 4A:
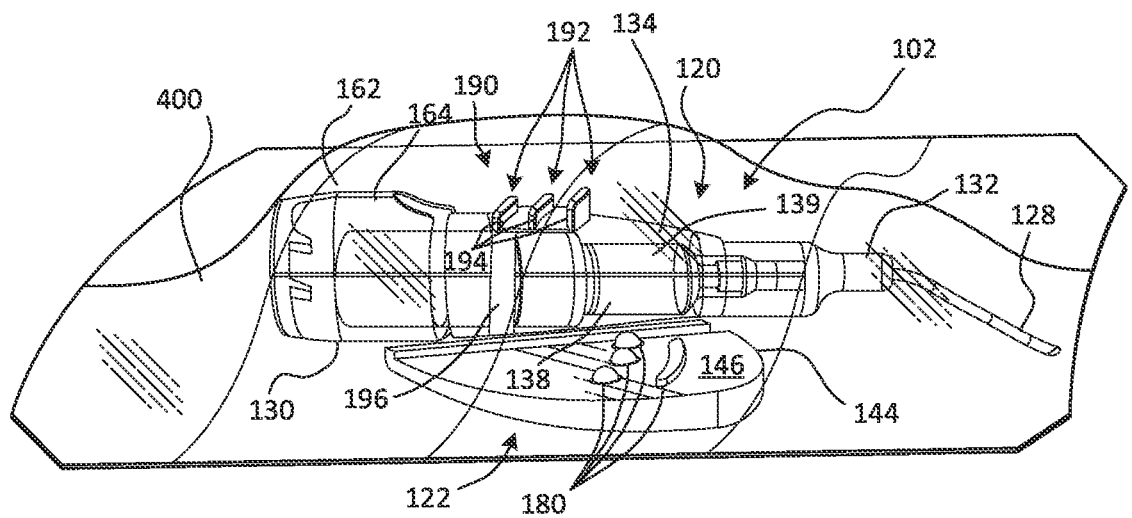
FIGS. 4A and 4B are perspective and side elevation views, respectively, of the catheter component of the IV catheter system of FIG. 1, positioned underneath a dressing.
Figure 4B:
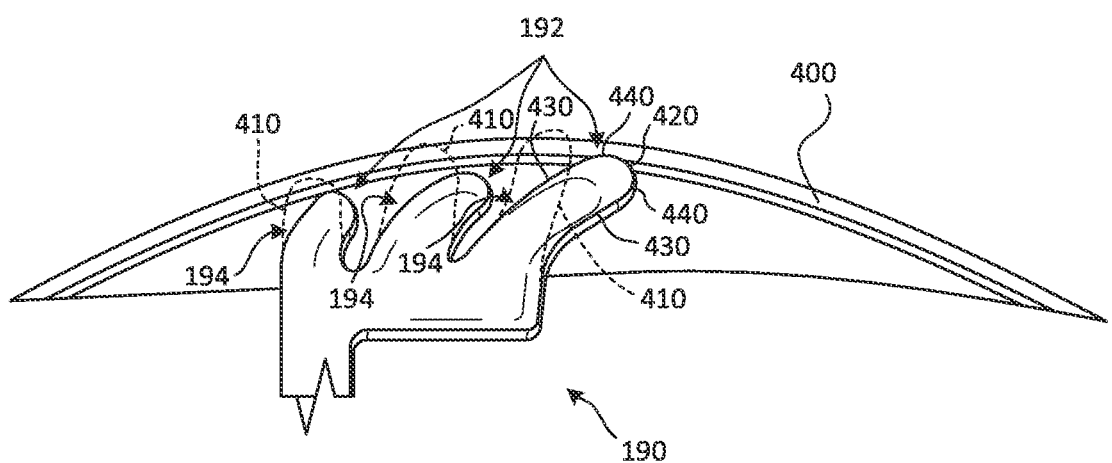

Referring to FIGS. 4A and 4B, perspective and side elevation views, respectively, depict the catheter component 102 of the IV catheter system 100 of FIG. 1, positioned underneath a dressing 400. The dressing 400 may be applied by a clinician to cover the catheter component 102 and/or hold it in place. Such dressings may, in some instances, be formed of a fabric or paper product that does not have a high puncture resistance. Further, the presence of protruding items may interfere with application and/or proper positioning of the dressing 400.

Accordingly, the tab 190 may beneficially be formed of a material having a relatively low durometer. It may be beneficial for the tab 190 to be formed of a material with a durometer lower than that of other portions of the catheter component 102, such as the translucent component 138. Thus, the catheter hub 120 may have the rigidity needed to help it perform its proper function, and the tab 190 may flex rather than abrading and/or puncturing the adjoining interior surface of the dressing 400.

Thus, in FIG. 4B, the tab 190 is depicted with the ridges 192 in a deflected condition. Specifically, the ridges 192 may bend proximally or distally; a distal bend is depicted in FIG. 4B. The undeflected positions 410 of the ridges 192 are depicted in phantom to illustrate how, in the undeflected state, the ridges 192 may protrude into the space occupied by the dressing 400, thereby risking damage to the dressing 400 and/or interference with application and/or proper positioning of the dressing 400.

Additionally or alternatively, the ridges 192 may be shaped to avoid puncture and/or abrasion of the dressing 400. For example, each of the ridges 192 may have an outer surface 420 and adjacent surfaces 430 that are adjacent to and angled relative to the outer surface 420. Further, each of the ridges 192 may have rounds 440 positioned to join each of the outer surfaces 420 with the adjacent surfaces 430 that surround it. The rounds 440 may define relatively blunt edges that help to protect the dressing 400. Thus, the geometry of the tab 190 may be selected to minimize the risk of puncture or abrasion of the dressing 400.

The tab 190 represents only one of a wide variety of push features that may be used in connection with the present disclosure. The ridges 192 are merely exemplary; in other embodiments, a tab or other push feature may have a variety of other features that facilitate gripping without damaging or interfering with a dressing. Such features may include, but are not limited to, differently-configured ridges, bumps, recesses, holes, stepped surfaces, textured surfaces, curved protruding surfaces, and the like. Any geometry that provides increased frictional engagement with a digit may be used as a push feature, or incorporated into a push feature.

Further, a wide variety of push features besides tabs may be used. According to one example, a circumferential ridge may be used as a push feature. For example, with reference to the IV catheter system 100 of FIGS. 1 through 4B, the catheter component 102 may be modified to omit the tab 190. The arms 196 may be extended to connect to each other, thereby encircling the catheter hub 120, or at least the portion of the catheter hub 120 that is not encircled by the securement platform 122. The resulting circumferential ridge may be thickened, textured, and/or otherwise further modified to enhance frictional engagement of the circumferential ridge with a user's digit. Thus, such a circumferential ridge may, itself, act as a push feature, and may provide flexibility by which a clinician may position a finger at any of various locations about the periphery of the catheter hub 120 to exert distal force on the catheter component 102.

A wide variety push features, aside from those specifically mentioned above, may be used. Various examples will be shown and described in connection with FIGS. 5 through 9B, as follows.

Figure 5:
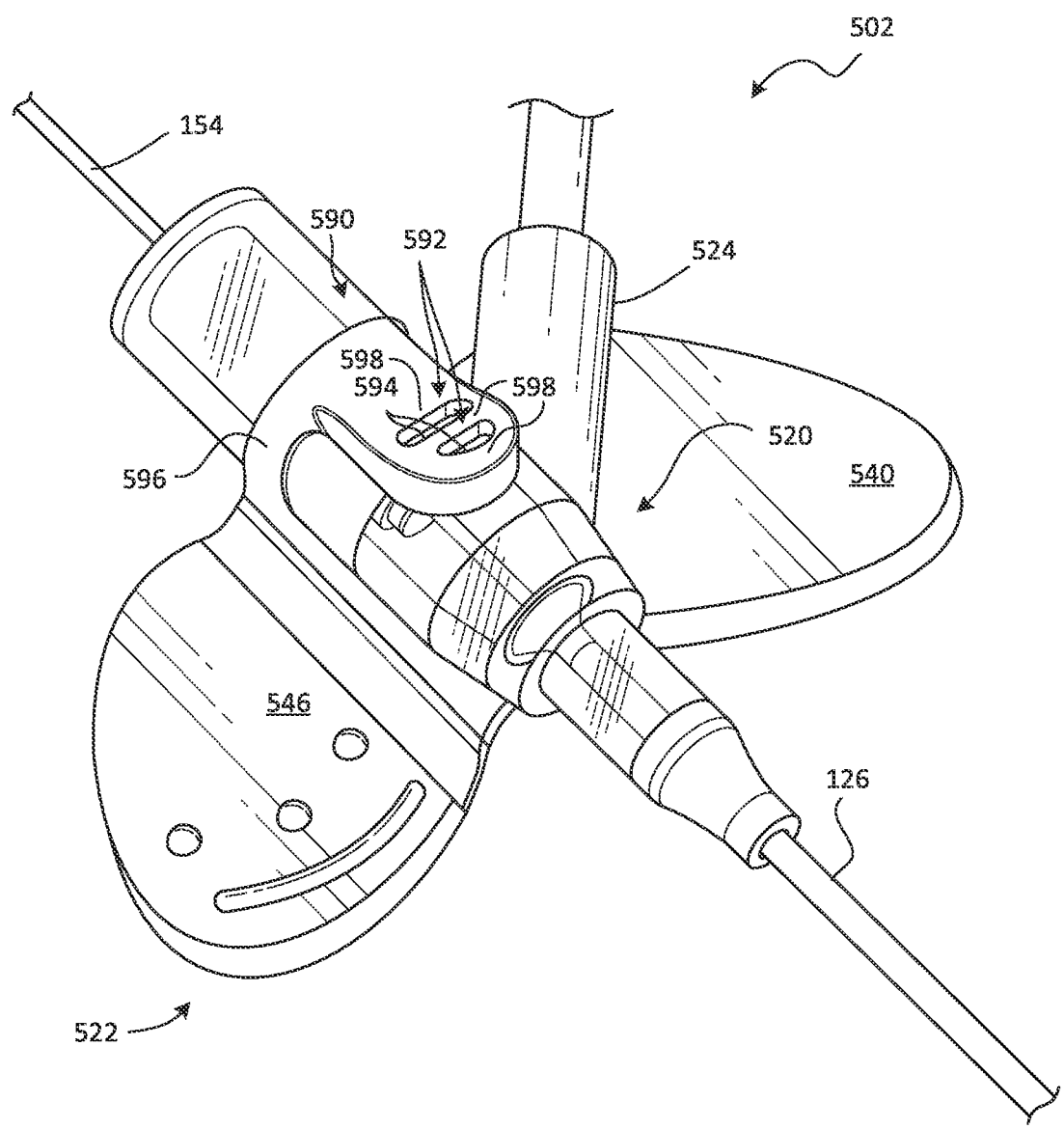
FIG. 5 is a perspective view of the needle and the catheter component of an IV catheter system according to one alternative embodiment.

Referring to FIG. 5, a perspective view depicts the needle 154 and the catheter component 502 of an IV catheter system according to one alternative embodiment. In addition to the catheter component 502, the IV catheter system may have components that generally correspond to those of the IV catheter system 100 of FIGS. 1 through 4B, such as a needle component, an extension tube, a clamp, a luer lock adapter, a flash receptacle, and/or other components. The catheter component 502 may have a configuration similar to that of the catheter component 102 of FIG. 1; however, some parts may be modified, added, or omitted to provide alternative ergonomics and/or functionality. Parts of the catheter component 502 that are not numbered or described may be assumed to have configurations and operational characteristics that are identical or similar to those of their counterparts of the catheter component 102 of FIGS. 1 through 4B.

As shown in FIG. 5, the catheter component 502 may have a catheter hub 520, a securement platform 522, an extension tubing junction 524, a cannula 126, and a tab 590. The securement platform 522 may have a first wing 540 and a second wing 546 that are shaped in a manner similar to the first wing 140 and the second wing 146 of the securement platform 122 of FIGS. 1 through 4B. The first wing 540 and the second wing 546 may be formed as single piece with each other and with the tab 590. The tab 590 may be connected to the securement platform 522 by a pair of arms 596 similar to the arms 196 of the catheter component 102 of FIGS. 1 through 4B.

The tab 590 may be shaped differently from the tab 190 of FIGS. 1 through 4B. Specifically, in place of ridges, the tab 590 may have a plurality of recesses 592. The interior of each recess may define a push feature 594, which may be the proximally-facing surface within each of the recesses 592. Outer surfaces 598 may exist between and around the recesses 592.

The tab 590 may function in a manner generally similar to that of the tab 190 of FIGS. 1 through 4B. Specifically, the push features 594 may receive contact from a digit, such as the finger 300 of FIG. 3. The contact may urge the catheter component 502 to move proximally, or to remain in position while the corresponding needle component (not shown) is withdrawn distally. The tab 590 may be formed of an elastomer or other low durometer material, and may thus provide a relatively gentle interface with the dressing 400. Further, the absence of ridges on the tab 590 may further help to avoid damage to the dressing 400. If desired, the edges between the outer surfaces 598 may be rounded to further help the tab 590 avoid abrading the dressing 400.

Figure 6A:
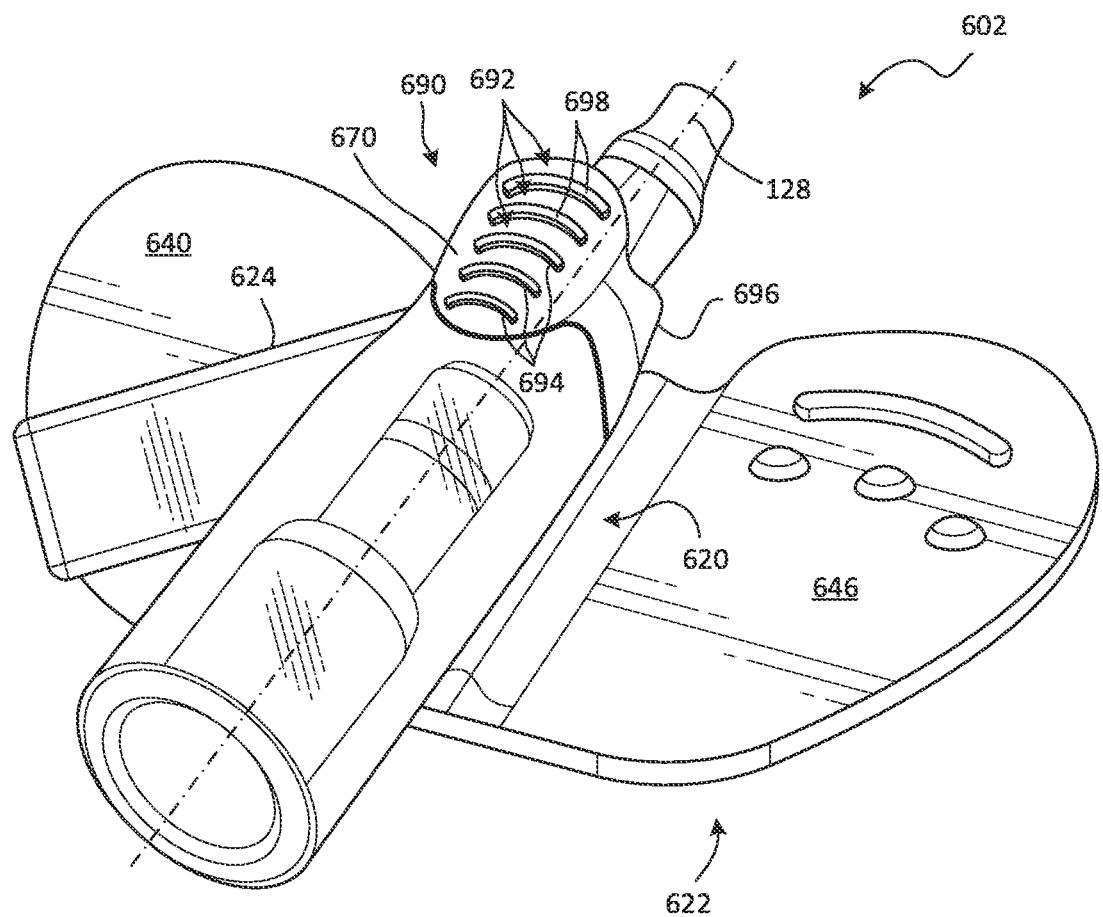
FIGS. 6A and 6B are perspective and side elevation views, respectively, of a catheter component of an IV catheter system according to another alternative embodiment.
Figure 6B:
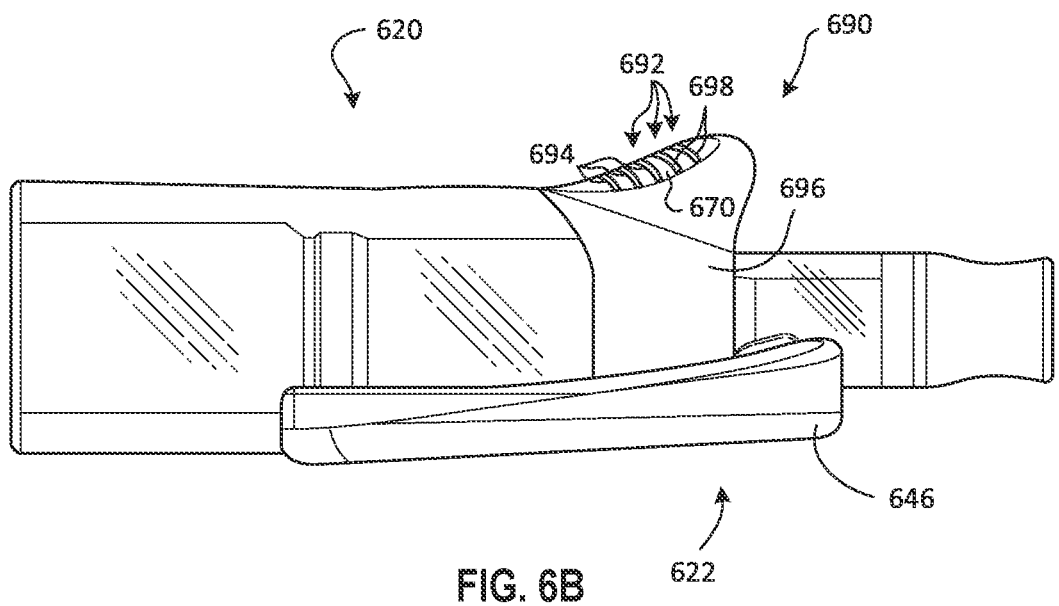

Referring to FIGS. 6A and 6B, a perspective view and a side elevation view, respectively, depict the catheter component 602 of an IV catheter system according to one alternative embodiment. In addition to the catheter component 602, the IV catheter system may have components that generally correspond to those of the IV catheter system 100 of FIGS. 1 through 4B, such as a needle component, an extension tube, a clamp, a luer lock adapter, a flash receptacle, and/or other components. The catheter component 602 may have a configuration similar to that of the catheter component 102 of FIG. 1; however, some parts may be modified, added, or omitted to provide alternative ergonomics and/or functionality. Parts of the catheter component 602 that are not numbered or described may be assumed to have configurations and operational characteristics that are identical or similar to those of their counterparts of the catheter component 102 of FIGS. 1 through 4B.

As shown in FIGS. 6A and 6B, the catheter component 602 may have a catheter hub 620, a securement platform 622, an extension tubing junction 624, a cannula (not shown), and a tab 690. The securement platform 622 may have a first wing 640 and a second wing 646 that are shaped in a manner similar to the first wing 140 and the second wing 146 of the securement platform 122 of FIGS. 1 through 4B. The first wing 640 and the second wing 646 may be formed as single piece with each other and with the tab 690. The tab 690 may be connected to the securement platform 622 by a pair of arms 696 similar to the arms 196 of the catheter component 102 of FIGS. 1 through 4B, and may optionally be formed as a single piece with the arms 696 and the securement platform 622.

The tab 690 may be positioned differently from the tab 190 of FIGS. 1 through 4B and the tab 590 of FIG. 5. Specifically, while the tab 190 and the tab 590 may be positioned generally equidistant from the distal and proximal ends of the catheter hub 120 and the catheter hub 520, respectively, the tab 690 of FIGS. 6A and 6B may be positioned proximate the distal end of the catheter hub 620. Thus, the tab 690 may provide for an alternative gripping arrangement and/or suitability for users with different anatomical characteristics (for example, longer fingers), by comparison with the tab 190 and the tab 590.

Further, the tab 690 may be shaped differently from the tab 190 of FIGS. 1 through 4B and the tab 590 of FIG. 5. Specifically, the tab 690 may have a plurality of ridges 692 that are somewhat thinner and shallower than the ridges 192 of the tab 190. The ridges 692 may have proximally-facing surfaces that define push features 694 that receive contact from the finger or thumb of the clinician. Each of the ridges 692 may have an outer surface 698, which may be joined to surrounding surfaces via rounds. Further, the tab 690 may have an underlying surface 670 that is angled nonparallel to a cannula axis 128 of the catheter component 602. The underlying surface 670 may be tilted such that the distal end of the underlying surface 670 is displaced further from the cannula axis 128 than the proximal end of the underlying surface 670. The orientation of the underlying surface 670 is more clearly visible in FIG. 6B.

The tab 690 may function in a manner generally similar to that of the tab 190 and the tab 590. Specifically, the push features 694 may receive contact from a digit, such as the finger 300 of FIG. 3. The contact may urge the catheter component 602 to move proximally, or to remain in position while the corresponding needle component (not shown) is withdrawn distally. The tab 690 may be formed of an elastomer or other low durometer material, as in previous embodiments.

Figure 7A:
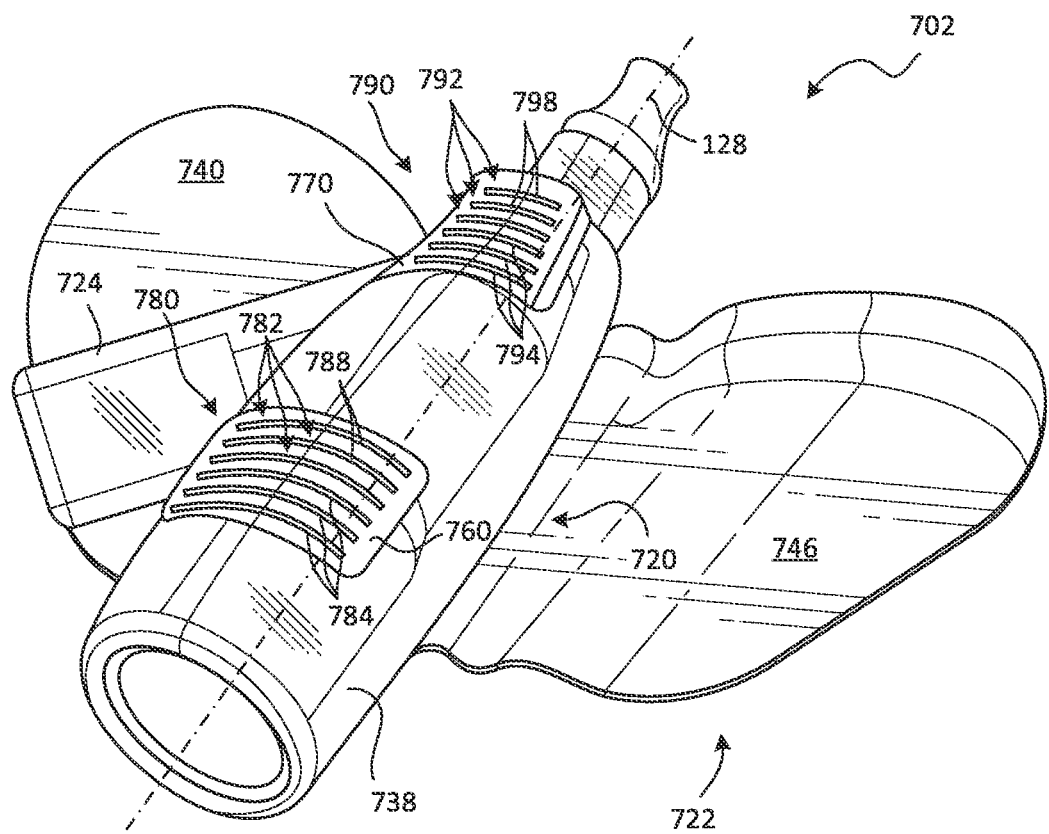
FIGS. 7A and 7B are perspective and side elevation views, respectively, of a catheter component of an IV catheter system according to another alternative embodiment.
Figure 7B:
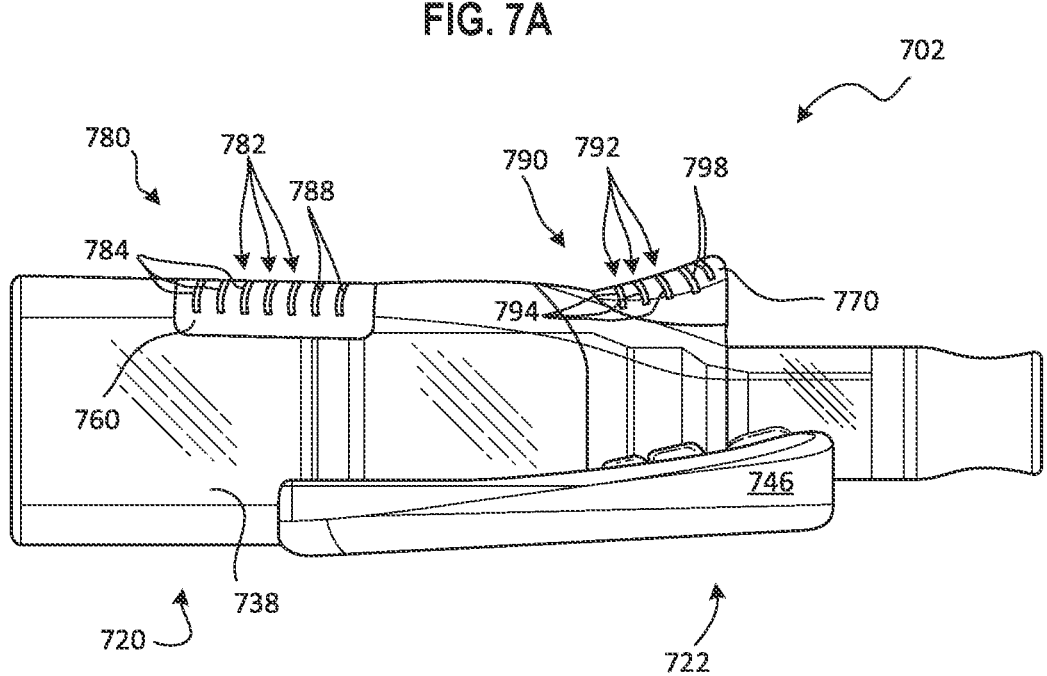

Referring to FIGS. 7A and 7B, a perspective view and a side elevation view, respectively, depict the catheter component 702 of an IV catheter system according to one alternative embodiment. In addition to the catheter component 702, the IV catheter system may have components that generally correspond to those of the IV catheter system 100 of FIGS. 1 through 4B, such as a needle component, an extension tube, a clamp, a luer lock adapter, a flash receptacle, and/or other components. The catheter component 702 may have a configuration similar to that of the catheter component 102 of FIG. 1; however, some parts may be modified, added, or omitted to provide alternative ergonomics and/or functionality. Parts of the catheter component 702 that are not numbered or described may be assumed to have configurations and operational characteristics that are identical or similar to those of their counterparts of the catheter component 102 of FIGS. 1 through 4B.

As shown in FIGS. 7A and 7B, the catheter component 702 may have a catheter hub 720, a securement platform 722, an extension tubing junction 724, a cannula (not shown), and a tab 790. The securement platform 722 may have a first wing 740 and a second wing 746 that are shaped in a manner similar to the first wing 140 and the second wing 146 of the securement platform 122 of FIGS. 1 through 4B. The first wing 740 and the second wing 746 may be formed as single piece with each other. However, the tab 790 may be formed separately from the securement platform 722. Particularly, the catheter hub 720 may have a translucent component 738 that defines most or all of the exterior surface of the catheter hub 720. The tab 790 may be secured to the translucent component 738 via chemical bonding, adhesive bonding, mechanical fastening, and/or the like.

The tab 790 may be positioned in a manner similar to that of the tab 690 of FIGS. 6A and 6B, toward the distal end of the catheter hub 720. The tab 790 may also have a configuration similar to that of the tab 690, with a plurality of ridges 792 that define push features 794 and outer surfaces 798. The tab 790 may also have an underlying surface 770 that is angled in a manner similar to that of the underlying surface 670 of FIGS. 6A and 6B, to facilitate the clinician's ability to urge the catheter component 702 to move distally, or to remain stationary when the corresponding needle hub (not shown) is withdrawn distally.

In addition to the tab 790, a pad 780 may also be secured to the translucent component 738 proximate the proximal end of the catheter hub 720. The pad 780 may have a shape generally similar to that of the tab 790, and may thus have a plurality of ridges 782 that provide push features 784 and outer surfaces 788. The pad 780 may also have an underlying surface 760 that lies generally flush with the surrounding portions of the translucent component 738. The pad 780 may provide supplemental gripping surfaces, allowing the clinician to easily grip the catheter component 702 with multiple fingers, or to exercise his or her preference regarding where to grip the catheter component 702 (for example, whether to grip the catheter component 702 toward the proximal end or the distal end of the catheter hub 720).

The tab 790 and/or the pad 780 may function in a manner generally similar to that of the tab 190, the tab 590, and the tab 690. Specifically, the push features 794 and/or the push features 784 may receive contact from a digit, such as the finger 300 of FIG. 3. The contact may urge the catheter component 702 to move proximally, or to remain in position while the corresponding needle component (not shown) is withdrawn distally. The tab 790 and/or the pad 780 may be formed of an elastomer or other low durometer material, as in previous embodiments.

Figure 8:
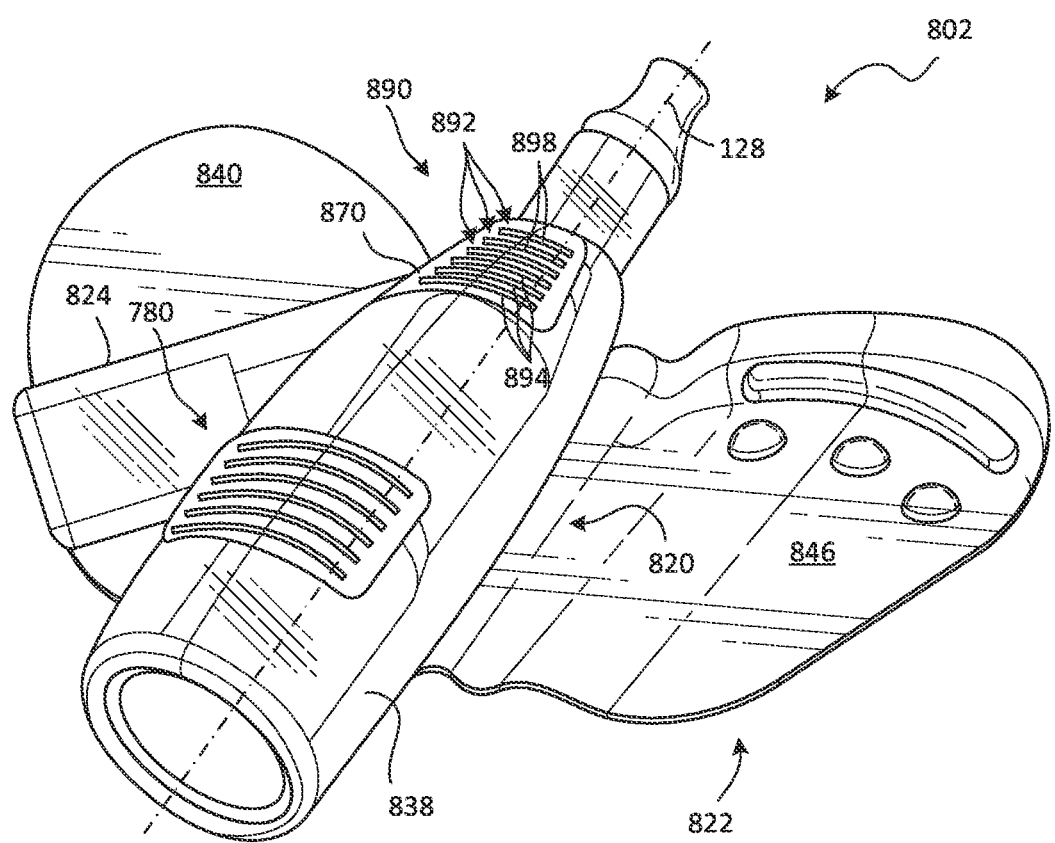
FIG. 8 is a perspective view of a catheter component of an IV catheter system according to another alternative embodiment.

Referring to FIG. 8, a perspective view depicts the catheter component 802 of an IV catheter system according to one alternative embodiment. In addition to the catheter component 802, the IV catheter system may have components that generally correspond to those of the IV catheter system 100 of FIGS. 1 through 4B, such as a needle component, an extension tube, a clamp, a luer lock adapter, a flash receptacle, and/or other components. The catheter component 802 may have a configuration similar to that of the catheter component 102 of FIG. 1; however, some parts may be modified, added, or omitted to provide alternative ergonomics and/or functionality. Parts of the catheter component 802 that are not numbered or described may be assumed to have configurations and operational characteristics that are identical or similar to those of their counterparts of the catheter component 102 of FIGS. 1 through 4B.

As shown in FIG. 8, the catheter component 702 may have a catheter hub 820, a securement platform 822, an extension tubing junction 824, a cannula (not shown), and a tab 890. The securement platform 822 may have a first wing 840 and a second wing 846 that are shaped in a manner similar to the first wing 140 and the second wing 146 of the securement platform 122 of FIGS. 1 through 4B. The first wing 840 and the second wing 846 may be formed as single piece with each other. However, like the tab 790 of FIGS. 7A and 7B, the tab 890 may be formed separately from the securement platform 822. Particularly, the catheter hub 820 may have a translucent component 838 that defines most or all of the exterior surface of the catheter hub 820. The tab 890 may be secured to the translucent component 838 via chemical bonding, adhesive bonding, mechanical fastening, and/or the like.

The tab 890 may be positioned in a manner similar to that of the tab 690 of FIGS. 6A and 6B and the tab 790 of FIGS. 7A and 7B, toward the distal end of the catheter hub 820. The tab 890 may also have a configuration similar to that of the tab 790, with a plurality of ridges 892 that define push features 894 and outer surfaces 898. The tab 890 may also have an underlying surface 870 that is angled in a manner different from that of the underlying surface 670 and the underlying surface 770. The underlying surface 870 may be angled such that the distal end of the underlying surface 870 is closer to the cannula axis 128 than the proximal end of the underlying surface 870. Thus, the underlying surface 870 may be substantially flush with the surrounding portions of the translucent component 838. Consequently, the underlying surface may not act as a push feature, but may provide the catheter component 802 with a relatively low profile that avoids interference with or damage to the dressing 400.

In addition to the tab 890, a pad 780 may also be secured to the translucent component 738 proximate the proximal end of the catheter hub 720. The pad 780 may have the same configuration and placement as in the catheter component 702 of FIGS. 7A and 7B. The presence of the pad 780 may help to compensate for the compact shape of the tab 890 by providing additional push features, as described in connection with FIGS. 7A and 7B.

The tab 890 and/or the pad 780 may function in a manner generally similar to that of the tab 190, the tab 590, the tab 690, the tab 790, and the pad 780. Specifically, the push features 894 and/or the push features 784 may receive contact from a digit, such as the finger 300 of FIG. 3. The contact may urge the catheter component 602 to move proximally, or to remain in position while the corresponding needle component (not shown) is withdrawn distally. The tab 890 and/or the pad 780 may be formed of an elastomer or other low durometer material, as in previous embodiments.

Figure 9A:
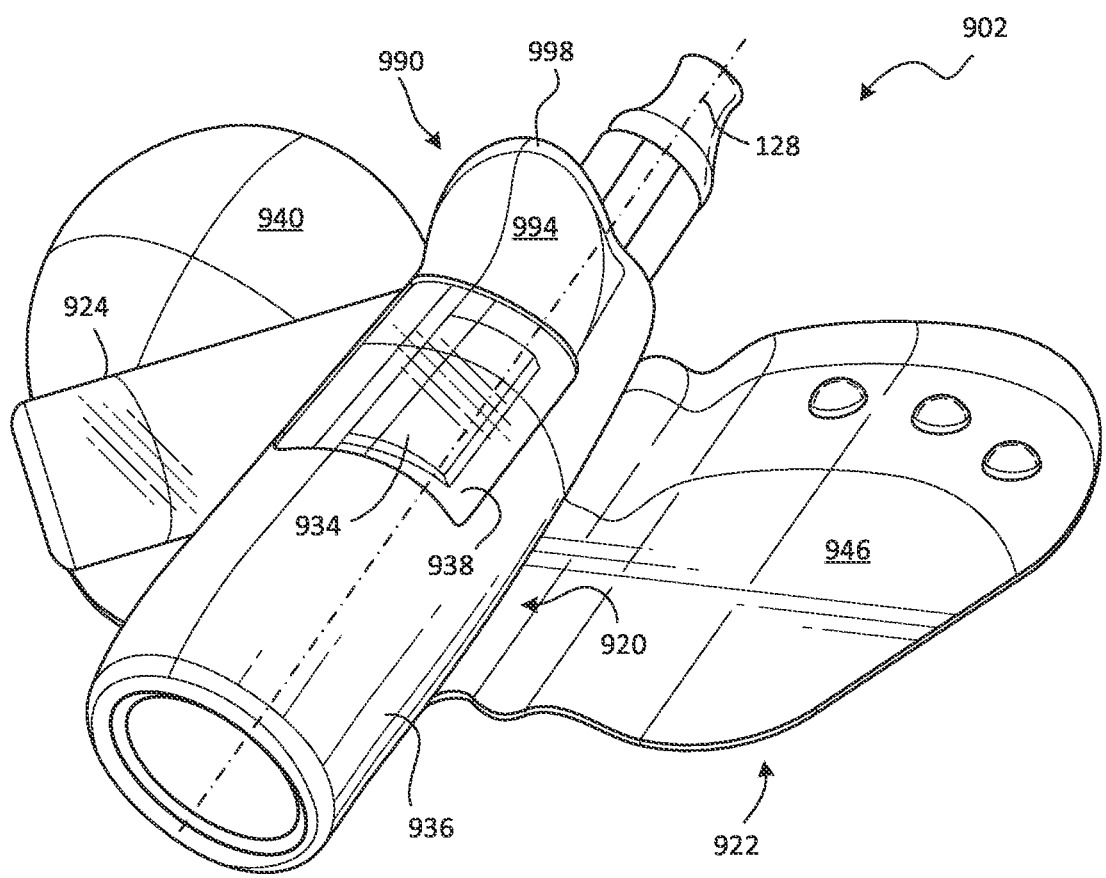
FIGS. 9A and 9B are perspective and side elevation views, respectively, of a catheter component of an IV catheter system according to yet another alternative embodiment.
Figure 9B:
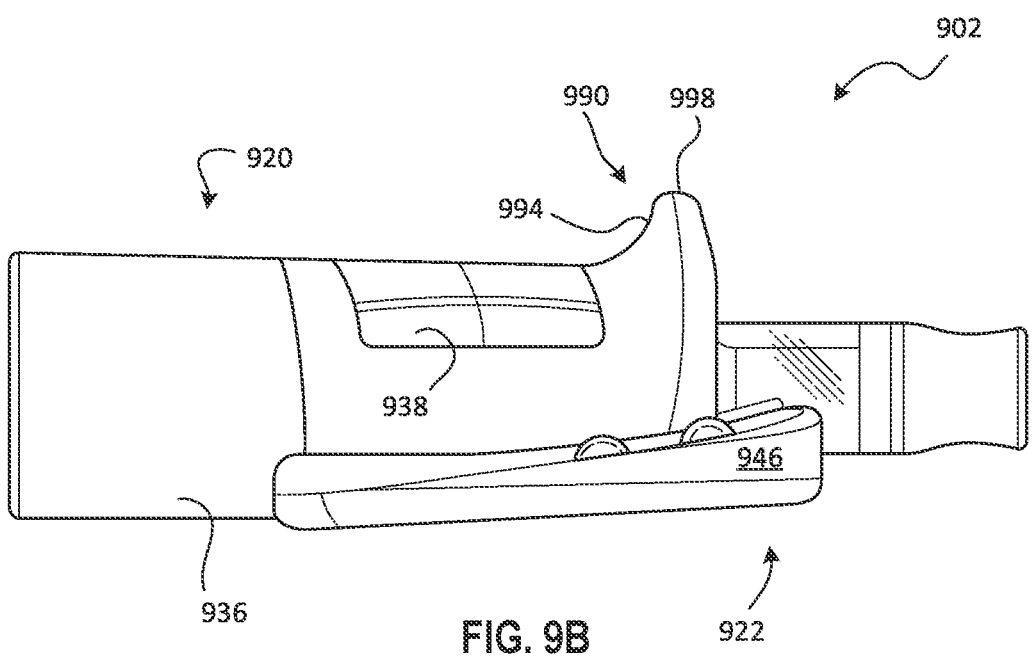

Referring to FIGS. 9A and 9B, a perspective view and a side elevation view, respectively, depict the catheter component 902 of an IV catheter system according to one alternative embodiment. In addition to the catheter component 902, the IV catheter system may have components that generally correspond to those of the IV catheter system 100 of FIGS. 1 through 4B, such as a needle component, an extension tube, a clamp, a luer lock adapter, a flash receptacle, and/or other components. The catheter component 902 may have a configuration similar to that of the catheter component 102 of FIG. 1; however, some parts may be modified, added, or omitted to provide alternative ergonomics and/or functionality. Parts of the catheter component 902 that are not numbered or described may be assumed to have configurations and operational characteristics that are identical or similar to those of their counterparts of the catheter component 102 of FIGS. 1 through 4B.

As shown in FIGS. 9A and 9B, the catheter component 902 may have a catheter hub 920, a securement platform 922, an extension tubing junction 924, a cannula (not shown), and a tab 990. The securement platform 922 may have a first wing 940 and a second wing 946 that are shaped in a manner similar to the first wing 140 and the second wing 146 of the securement platform 122 of FIGS. 1 through 4B. The first wing 940 and the second wing 946 may be formed as single piece with each other.

The tab 990 may optionally be formed separately from the securement platform 922. The catheter hub 920 may have an opaque component 936 that defines the majority of the exterior surface of the catheter hub 920, and a translucent component 938 that provides a window into a chamber 934 defined within the catheter hub 920, enabling the clinician to see into the chamber 934. The tab 990 may be formed as a single piece with the opaque component 936. Thus, the tab 990 and the opaque component 936 may both be formed of a low durometer material such as an elastomer. If desired, the securement platform 922 may be formed as a single piece with the tab 990 and the opaque component 936.

The tab 990 may be positioned in a manner similar to that of the tab 690, the tab 790, and the tab 890 of FIGS. 6A through 8, toward the distal end of the catheter hub 920. However, the tab 990 may have a very simple shape, without the distinct ridges of the other embodiments. Rather, the tab 990 may rise from the catheter hub 920 in a relatively steep angle to define a single outer surface 998. The tab 990 may define a single push feature 994 of substantial size. Thus, the tab 990 may facilitate the clinician's ability to urge the catheter component 702 to move distally, or to remain stationary when the corresponding needle hub (not shown) is withdrawn distally. The relatively simple design of the tab 990 may help avoid abrasion against the dressing 400. Further, as mentioned previously, the tab 990 may be formed of a low durometer material such as an elastomer. This may enable the tab 990 to bend under the dressing 400, like the tab 190 in FIG. 4B.

The tab 990 may function in a manner generally similar to that of the tab 190, the tab 590, the tab 690, the tab 790, the pad 780, and the tab 890. Specifically, the push feature 994 may receive contact from a digit, such as the finger 300 of FIG. 3. The contact may urge the catheter component 902 to move proximally, or to remain in position while the corresponding needle component (not shown) is withdrawn distally.

Figure 10:
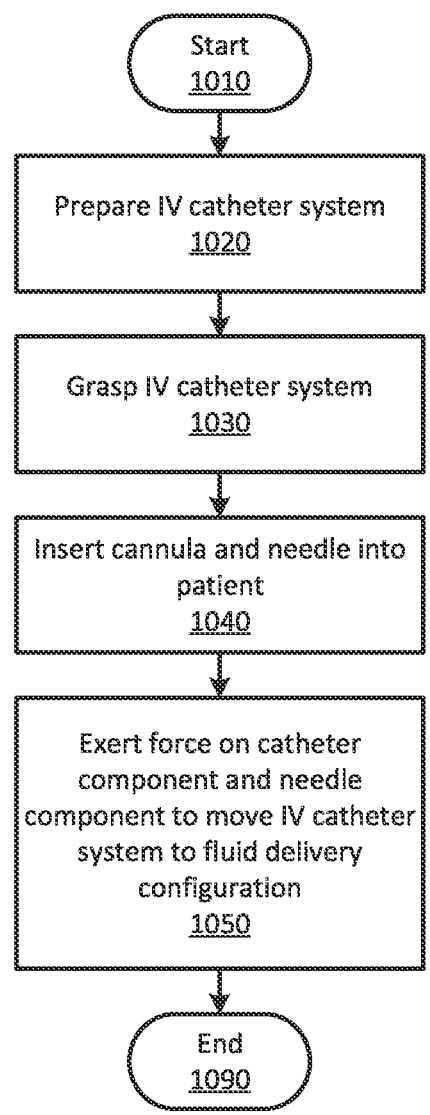
FIG. 10 is a flowchart diagram depicting one method of preparing an IV catheter system to deliver fluid to a patient, according to one embodiment.

Referring to FIG. 10, a flowchart diagram depicts one method of preparing an IV catheter system to deliver fluid to a patient, according to one embodiment. The method of FIG. 10 may be carried out with any of the IV catheter systems disclosed in FIG. 1 through 9B, or with other IV catheter system embodiments that are not specifically shown or described herein. By way of example, the method will be described in connection with the IV catheter system 100 of FIG. 1. Further, the method of FIG. 10 is merely exemplary; other methods may be used in conjunction with any of the IV catheter system embodiments included within the scope of the present disclosure.

The method may start 1010 with a step 1020 in which the IV catheter system 100 is prepared. This preparation may include connecting various components (such as the catheter component 102, the needle component 104, the extension tube 106, the clamp 108, and/or the Y adapter 110 of FIG. 1, by way of example) together. Further, this may include preparing any adhesives or dressings, such as the dressing 400 of FIGS. 4A and 4B, needed to secure the catheter component 102 to the patient.

In a step 1030, the IV catheter system 100 may be grasped. This may be done with both hands, or optionally, with a single hand. This may involve placing digits of the hand to contact the pull surface(s) of the needle component 104 and the push feature(s) of the catheter component 102, as described above. Notably, the surfaces that serve as pull surfaces and push features may vary, depending on the specific embodiment utilized. Further, catheter insertion may involve primarily pushing; accordingly, the clinician may elect not to make contact with the pull surfaces at this stage, but to contact them when the IV catheter system 100 is to be moved to the fluid delivery configuration.

In a step 1040, the IV catheter system 100 may be manipulated to insert the cannula 126 into the patient. This may be done with both hands, or optionally, with a single hand. Insertion may continue until the tip of the cannula 126 has reached the fluid delivery location. Insertion may be carried out by pushing on the push features and/or other surfaces of the catheter component 102 and/or the needle component 104. The clinician may confirm proper insertion of the cannula 126 by observing blood flow into the chamber 134, through the wall provided by the translucent component 138.

In a step 1050, the IV catheter system 100 may be moved from the insertion configuration to the fluid delivery configuration. If the clinician has not yet contacted the pull surface(s) of the needle component 104, he or she may do this now with one or more digits of a hand. Optionally, the same hand used to insert the IV catheter system 100 may be used, exclusively (i.e., without assistance from the other hand) to move the IV catheter system 100 to the fluid delivery configuration. The clinician may pull the pull surface(s) proximally, while pushing on the push feature(s) to keep the catheter component 102 in place. Thus, the catheter component 102 may be kept in place with the tip of the cannula 126 at the fluid delivery location while the needle component 104 is withdrawn proximally from the catheter component 102 to unblock the fluid delivery path to the fluid delivery location.

This may optionally be accomplished with a single hand. Thus, the other hand may be used to perform other tasks during insertion and/or motion of the IV catheter system 100 to the fluid delivery configuration. For example, the clinician may use the other hand to hold the patient's arm (or other body part in which the fluid delivery location is located), prepare other components for interconnection with the IV catheter system 100, prepare any necessary blood testing materials, and/or the like.

The method may then end 1090. With the IV catheter system 100 in the fluid delivery configuration, the fluid source may then be connected to the catheter component 102 to deliver the fluid to the patient.

In some embodiments, a catheter IV system, such as, for example, the catheter IV systems of any of FIGS. 1-9B, may include a needle safety mechanism. The needle safety mechanism may include any safety mechanism configured to secure a sharpened, distal tip of an introducer needle, such as the needle 154, when the needle is withdrawn from a catheter of the particular catheter device, preventing accidental needle sticks.

The safety mechanism may be coupled with the catheter IV system in any number of ways. In some embodiments, the safety mechanism may include an internal interlock in which the safety mechanism is coupled with an internal surface of a catheter component. Coupling may include threading, fitting, snapping, connecting, attaching, fastening, clipping, hooking, or any other suitable means of coupling. Non-limiting examples of safety mechanisms that include an internal interlock are provided in: U.S. Pat. No. 8,496,623, titled BI-DIRECTIONAL CANNULA FEATURE CAPTURE MECHANISM, filed Mar. 2, 2009; U.S. Pat. No. 9,399,120, titled BI-DIRECTIONAL CANNULA FEATURE CAPTURE MECHANISM, filed Jul. 11, 2013; U.S. Patent Application No. 62/314,262, titled CANNULA CAPTURE MECHANISM, filed Mar. 28, 2016, each of which is herein incorporated by reference in its entirety. In some embodiments, the safety mechanism may include a clip disposed within the catheter component, a non-limiting example of which is provided in U.S. Pat. No. 6,117,108, titled SPRING CLIP SAFETY IV CATHETER, filed Jun. 12, 1998, which is herein incorporated by reference in its entirety.

In some embodiments, the safety mechanism may include an external interlock in which the safety mechanism is coupled with an external surface of the catheter component. In some embodiments, the safety mechanism may be coupled with an external surface of the catheter component and an internal and/or external surface of a needle hub. Coupling may include threading, fitting, snapping, connecting, attaching, fastening, clipping, hooking, or any other suitable means of coupling. Non-limiting examples of safety mechanisms that include an external interlock are provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. In some embodiments, the safety mechanism may include a V-clip or a similar clip. A non-limiting example of a V-clip is provided in U.S. patent application Ser. No. 14/295,953, titled PORTED IV CATHETER HAV- ING EXTERNAL NEEDLE SHIELD AND INTERNAL BLOOD CONTROL SEPTUM, filed Jun. 4, 2014, which is herein incorporated by reference in its entirety. The V-clip may selectively retain a portion of the catheter adapter.

In some embodiments, a defeatable mechanical connection is provided between the safety mechanism and at least one other component of the IV catheter system. In some instances, the mechanical connection is defeated upon securement of the distal tip of the needle within the safety mechanism. In some embodiments, a surface of the safety mechanism is selectively coupled to one or more of the following: the catheter component, a blood control valve, an extension tube, and one or more grips.

In some embodiments, the safety mechanism may include a safety barrel, which may be spring-loaded. For example, the safety barrel may be spring loaded as in the BD™ Insyte® Autoguard™ BC shielded protective IV catheter. In some embodiments, the safety mechanism may be passively and/or actively activated. In some embodiments, the safety mechanism may be configured to interact with a needle feature, such as a ferrule, notch, crimp or bump on the needle. In some embodiments, the safety mechanism may include an arm or lever that may be actuated to capture the distal tip within the safety mechanism and prevent the tip from emerging prior to safe disposal. In some embodiments, the safety mechanism may be attached to a body of the needle and may be capable of sliding along the length thereof.

In some embodiments, in an assembled position prior to catheterization, the safety mechanism may be disposed between the catheter adapter and the needle hub. In some embodiments, the catheter adapter and the needle hub may be spaced apart by at least a portion of the safety mechanism in the assembled position prior to catheterization. In some embodiments, in the assembled position prior to catheterization, a proximal end of the catheter adapter may be disposed between a distal end of the safety mechanism and a distal end of a grip of the needle hub, such as, for example, a grip. In some embodiments, in the assembled position prior to catheterization, the proximal end of the catheter component may be disposed between the distal end of the safety mechanism and a proximal end of the grip of the needle hub. In some embodiments, a portion of the safety mechanism may overlap with a portion of the grip of the needle hub. In some embodiments, at least a portion of at least one of the catheter component and the grip overlaps at least some portion of the safety mechanism. In some embodiments, no portion of the catheter adapter body or the grip overlaps any portion of the safety mechanism.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

We claim:

1. An IV catheter system comprising an insertion configuration and a fluid delivery configuration, the IV catheter system comprising:
 a catheter component comprising:
  a catheter hub comprising a catheter hub distal end and a catheter hub proximal end, wherein the catheter hub is shaped to define a chamber extending between the catheter hub distal end and the catheter hub proximal end, and a needle port at the catheter hub proximal end that provides access to the chamber;
  a cannula extending distally from the catheter hub distal end along a cannula axis; and
  a push feature extending outward from the catheter hub, wherein the push feature comprises an outer surface positioned to receive contact from a digit such that the digit urges the IV catheter system to move from the insertion configuration to the fluid delivery configuration; and
 a needle component comprising:
  a needle hub comprising a needle hub distal end and a needle hub proximal end; and
  a needle extending distally from the needle hub distal end along a needle axis;
 wherein, in the insertion configuration, the needle is positioned within the cannula and the needle hub distal end is seated in the needle port;
 wherein, in the fluid delivery configuration, the needle is positioned outside the catheter hub;
 wherein the push feature is formed of a flexible material that causes the push feature, in response to pressure exerted on the outer surface by a dressing securing the catheter component to a patient, to flex such that the outer surface deflects toward the cannula axis.

2. The IV catheter system of claim 1, wherein:
 the needle component further comprises a grip extending from the needle hub, generally parallel to the needle axis, the grip comprising a pull feature; and
 the push feature and the pull feature are positioned to receive contact from one or more additional digits of the same hand as the digit to urge the IV catheter system to move from the insertion configuration to the fluid delivery configuration.

3. The IV catheter system of claim 2, wherein the catheter component further comprises a securement platform comprising a first wing extending from the catheter hub, generally parallel to the cannula axis such that, in the fluid delivery configuration, the first wing rests on skin of a patient receiving fluid through the IV catheter system.

4. The IV catheter system of claim 3, wherein:
 in the insertion configuration, the first wing and the grip are generally parallel to each other and are positioned in abutting relation to each other; and
 during motion of the IV catheter system from the insertion configuration to the fluid delivery configuration, the grip slides along the first wing.

5. The IV catheter system of claim 1, wherein the push feature comprises a tab positioned closer to the catheter hub distal end than to the catheter hub proximal end.

6. The IV catheter system of claim 5, wherein the catheter component further comprises a pad positioned proximate the catheter hub proximal end, wherein the pad comprises a surface texture selected to provide frictional engagement with the digit or with another digit of the same hand as the digit.

7. The IV catheter system of claim 1, wherein the push feature comprises a tab positioned generally equidistant from the catheter hub distal end and the catheter hub proximal end.

8. The IV catheter system of claim 1, wherein the outer surface is on a first ridge oriented substantially perpendicular to the cannula axis.

9. The IV catheter system of claim 8, wherein the push feature further comprises a plurality of additional ridges oriented generally parallel to the first ridge.

10. The IV catheter system of claim 1, wherein the push feature is formed of a material having a lower durometer than the catheter hub.

11. The IV catheter system of claim 1, wherein the catheter hub further comprises an opaque component molded as a single piece with the push feature.

12. The IV catheter system of claim 11, wherein the catheter hub further comprises a translucent component defining at least one wall of the chamber such that blood within the chamber is visible from outside the chamber through the at least one wall.

13. The IV catheter system of claim 1, wherein the push feature comprises:
 a plurality of adjacent surfaces adjacent to and angled relative to the outer surface; and
 a plurality of rounds positioned to join the outer surface with each of the adjacent surfaces in a manner that avoids puncturing the dressing.

14. An IV catheter system comprising an insertion configuration and a fluid delivery configuration, the IV catheter system comprising:
 a catheter component comprising:
  a catheter hub comprising a catheter hub distal end and a catheter hub proximal end, wherein the catheter hub further comprises:
   a translucent component defining at least one wall of a chamber extending between the catheter hub distal end and the catheter hub proximal end; and
   a needle port at the catheter hub proximal end that provides access to the chamber;
  a cannula extending distally from the catheter hub distal end along a cannula axis; and
  a tab extending outward from the catheter hub, wherein the tab is formed of a material having a lower durometer than the translucent component; and
 a needle component comprising:
  a needle hub comprising a needle hub distal end and a needle hub proximal end; and
  a needle extending distally from the needle hub distal end along a needle axis;
 wherein, in the insertion configuration, the needle is positioned within the cannula and the needle hub distal end is seated in the needle port;
 wherein, in the fluid delivery configuration, the needle is positioned outside the catheter hub.

15. The IV catheter system of claim 14, wherein:
 the needle component further comprises a grip extending from the needle hub, generally parallel to the needle axis, the grip comprising a pull feature;
 the tab and the pull feature are positioned to receive contact from one or more digits of a single hand to urge the IV catheter system to move from the insertion configuration to the fluid delivery configuration;
 the catheter component further comprises a securement platform comprising a first wing extending from the catheter hub, generally parallel to the cannula axis such that, in the fluid delivery configuration, the first wing rests on skin of a patient receiving fluid through the IV catheter system;
 in the insertion configuration, the first wing and the grip are generally parallel to each other and are positioned in abutting relation to each other; and
 during motion of the IV catheter system from the insertion configuration to the fluid delivery configuration, the grip slides along the first wing.

16. The IV catheter system of claim 14, wherein the tab comprises:
 an outer surface positioned to receive contact from a digit such that the digit urges the IV catheter system to move from the insertion configuration to the fluid delivery configuration;
 a plurality of adjacent surfaces adjacent to and angled relative to the outer surface; and
 a plurality of rounds positioned to join the outer surface with each of the adjacent surfaces in a manner that avoids puncturing a dressing securing the catheter component to a patient.

17. The IV catheter system of claim 14, wherein the catheter hub further comprises an opaque component formed as a single piece with the tab such that the opaque component cooperates with the translucent component to define the chamber.

18. An IV catheter system comprising an insertion configuration and a fluid delivery configuration, the IV catheter system comprising:
 a catheter component comprising:
  a catheter hub comprising a catheter hub distal end and a catheter hub proximal end, wherein the catheter hub is shaped to define a chamber extending between the catheter hub distal end and the catheter hub proximal end, and a needle port at the catheter hub proximal end that provides access to the chamber;
  a cannula extending distally from the catheter hub distal end along a cannula axis; and
  a push feature extending outward from the catheter hub, wherein the push feature comprises:
   an outer surface positioned to receive contact from a digit such that the digit urges the IV catheter system to move from the insertion configuration to the fluid delivery configuration;
   a plurality of adjacent surfaces adjacent to and angled relative to the outer surface; and
   a plurality of rounds positioned to join the outer surface with each of the adjacent surfaces in a manner that avoids puncturing a dressing securing the catheter component to a patient; and
 a needle component comprising:
  a needle hub comprising a needle hub distal end and a needle hub proximal end;
  a needle extending distally from the needle hub distal end along a needle axis; and
  a grip extending from the needle hub, generally parallel to the needle axis, the grip comprising a pull feature;
 wherein, in the insertion configuration, the needle is positioned within the cannula and the needle hub distal end is seated in the needle port;
 wherein, in the fluid delivery configuration, the needle is positioned outside the catheter hub;
 wherein the push feature is formed of a flexible material that causes the push feature, in response to pressure exerted on the outer surface by the dressing, to flex such that the outer surface deflects toward the cannula axis;
 wherein the push feature and the pull feature are positioned to receive contact from one or more additional digits of the same hand as the digit to urge the IV catheter system to move from the insertion configuration to the fluid delivery configuration;
 wherein the catheter component further comprises a securement platform comprising a first wing extending from the catheter hub, generally parallel to the cannula axis such that, in the fluid delivery configuration, the first wing rests on skin of a patient receiving fluid through the IV catheter system;

wherein, in the insertion configuration, the first wing and the grip are generally parallel to each other and are positioned in abutting relation to each other;

wherein, during motion of the IV catheter system from the insertion configuration to the fluid delivery configuration, the grip slides along the first wing;

wherein the push feature is formed of a material having a lower durometer than the catheter hub.

19. The IV catheter system of claim 18, wherein:

the push feature comprises a tab positioned closer to the catheter hub distal end than to the catheter hub proximal end; and the catheter component further comprises a pad positioned proximate the catheter hub proximal end, wherein the pad comprises a surface texture selected to provide frictional engagement with the digit or with another digit of the same hand as the digit.

20. The IV catheter system of claim 18, wherein the catheter hub further comprises:

an opaque component molded as a single piece with the push feature; and a translucent component defining at least one wall of the chamber such that blood within the chamber is visible from outside the chamber through the at least one wall.

* * * * *